Jan. 8, 1963 M. G. HENRY Plant Pat. 2,212
BARBERRY PLANT
Filed March 1, 1962
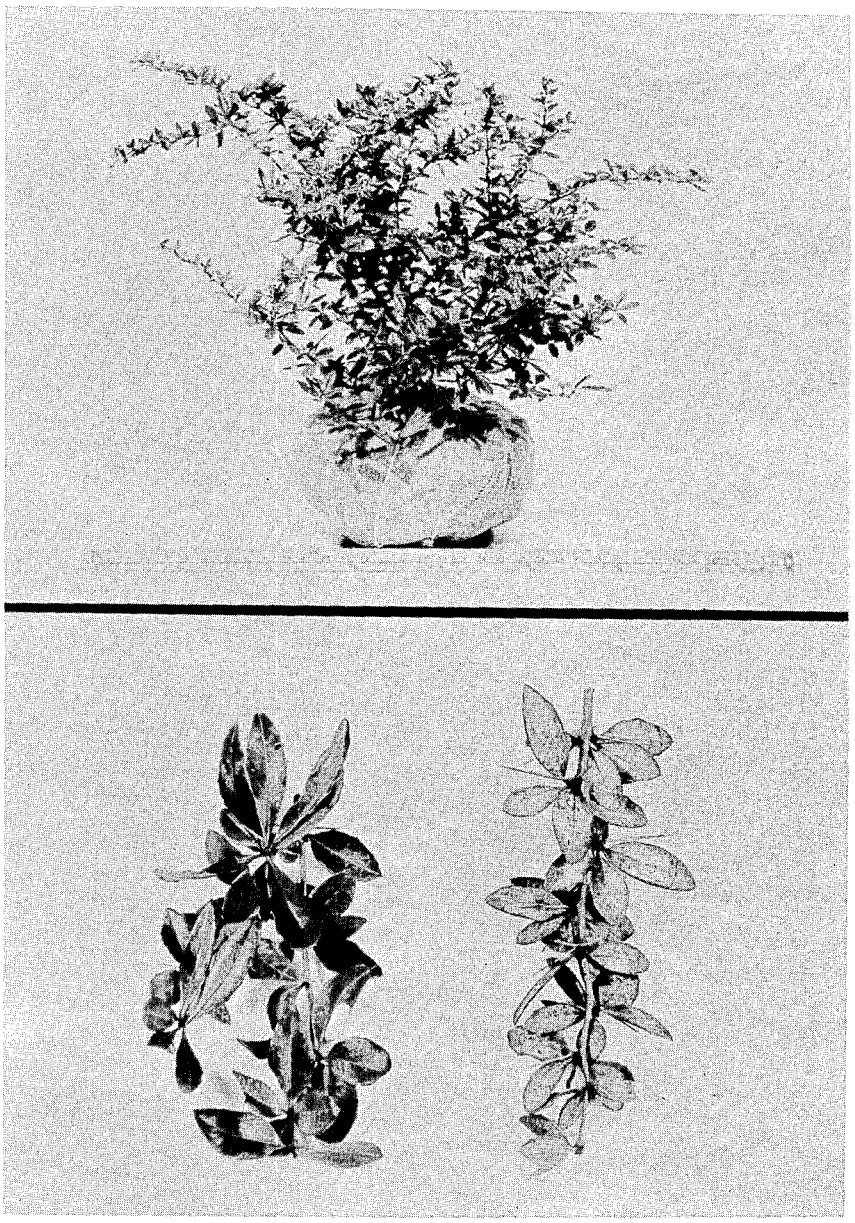
Inventor.
Mary G. Henry
By: Robb & Robb
Attorneys.

United States Patent Office

Plant Pat. 2,212
Patented Jan. 8, 1963

2,212
BARBERRY PLANT

Mary G. Henry, Gladwyne, Pa., assignor to Styer's Nurseries, Concordville, Pa., a partnership Filed Mar. 1, 1962, Ser. No. 176,836
1 Claim. (Cl. 47—59)

The present invention relates to a new and distinct variety of barberry plant of the evergreen class, which originated as a selected seedling produced by me by deliberately planting seed on my cultivated property at Gladwyne, in the county of Montgomery, and State of Pennsylvania.

At the time of my origination aforesaid, there was growing in my arboretum at Gladwyne, Pennsylvania, a barberry plant which I believed to be of a hybrid nature because it began growing as a seedling beneath a plant of the species *Berberis verruculosa* (unpatented), yet differed markedly from that species. In the course of plant breeding at my arboretum, seeds from this hybrid were harvested and sown by me, and from the seedlings thus produced, the new variety which is the subject hereof was derived and selected as a second generation seedling of a putative hybrid of which *Berberis verruculosa* was probably the seed parent and *Berberis julianae* (unpatented) may be the pollen parent.

Asexual reproductions of the new variety were made by me by rooted cuttings in the course of studies and tests in my trial garden at Concordville, Pennsylvania. Prolonged and continuous observations of the original selected seedling and the various progeny thereof derived from the asexual reproductions aforesaid, convinced me that my selected seedling was a new and distinct variety, and definitely distinguishable from all other Berberis varieties, as evidenced by the following unique combination of characteristics which are outstanding therein and which distinguish it from its parents, as well as from all other varieties of which I am aware:

(1) An evergreen habit;

(2) A plant form falling between the species *B. verruculosa* and *B. julianae,* said form being particularly characterized by a low-growing habit (averaging about 3 feet in height) with many stems extending from the ground, and the branches arching and eventually drooping, but not rooting in the ground;

(3) Attractive foliage generally similar to that of the species *B. julianae,* but of smaller size; and (4) A more vigorous and more rapid growing habit than the species *B. verruculosa.*

The accompanying drawing shows a typical specimen plant of my new barberry variety, as well as specimens of the foliage as seen from the upper and lower surfaces thereof, the latter foliage views being depicted on an enlarged scale to better disclose the details thereof.

The following is a detailed description of the new variety, with color terminology in accordance with the Nickerson Color Fan, published by Munsell Color Company, Inc., of Baltimore, Maryland, except where general color terms of ordinary dictionary significance are obvious, as based upon specimens grown at Concordville, Pennsylvania:

Parentage: Second generation seedling of a putative hybrid of *Berberis verruculosa* and *Berberis julianae,* the latter being the probable male parent of the hybrid.

Propagation: Holds its distinguishing characteristics through succeeding propagations by rooted cuttings.

Plant:

*Growth.*—Vigorous; relatively rapid; low-growing.

*Branches.*—Arching and eventually drooping, but not rooting in the ground. Bark—ribbed. Color (mature wood)—yellowish-green.

*Stems.*—Bear 3-spined thorns at the nodes and ranging from about ½ inch to 1 inch long and being generally similar to the thorns of *B. julianae,* but smaller at the nodes. Color—light yellowish-brown.

*Foliage.*—Generally similar to that of *B. julianae,* but somewhat smaller; persistent until April; glossy; leathery; extremely sharply spined on the edges; setae up to 1/16 inch long and up to 20 in number. Borne—on short branches forming in the axils of the thorns, in groups of from 3 to 12. Shape—oval. Size: length—from about ¾ inch to about 3½ inches; width—from about ½ inch to about ¾ inch. Color: upper side—Glossy Moderate Yellow Green, Plate 7.5GY 5/7, changing in winter to Dark Red, Plate 5R 3/7; under side—Moderate Yellow Green, Plate 5GY 5/6, with patches of white bloom.

Flowers: Borne in fascicles of from 6 to 10; larger in size than those of *B. verruculosa* and usually more numerous.

Fruit: Color—dark blue berry.

I claim:

A new and distinct variety of barberry plant of the evergreen class, substantially as herein shown and described, characterized particularly as to novelty by the unique combination of a vigorous, relatively rapid but low-growing habit of growth, with many stems extending from the ground and branches arching and eventually drooping but not rooting in the ground, and said branches bearing leaves generally similar to those of the species *B. julianae* (unpatented) but of smaller size.

No references cited.